US009494542B2

(12) United States Patent
Novac

(10) Patent No.: US 9,494,542 B2
(45) Date of Patent: Nov. 15, 2016

(54) CONTROL SYSTEM AND METHOD FOR SENSOR MANAGEMENT

(71) Applicant: EM Microelectronic-Marin SA, Marin (CH)

(72) Inventor: Pinchas Novac, Neuchatel (CH)

(73) Assignee: EM Microelectronic-Marin SA, Marin (CH)

( * ) Notice: Subject to any disclaimer, the term of this patent is extended or adjusted under 35 U.S.C. 154(b) by 311 days.

(21) Appl. No.: 14/155,630

(22) Filed: Jan. 15, 2014

(65) Prior Publication Data

US 2014/0197849 A1   Jul. 17, 2014

(30) Foreign Application Priority Data

Jan. 17, 2013  (EP) ..................................... 13151668

(51) Int. Cl.
| | |
|---|---|
| *G01R 27/28* | (2006.01) |
| *G01N 27/02* | (2006.01) |
| *G01N 27/22* | (2006.01) |
| *G01D 5/24* | (2006.01) |
| *G01D 5/243* | (2006.01) |
| *G01N 27/04* | (2006.01) |

(52) U.S. Cl.
CPC .............. *G01N 27/028* (2013.01); *G01D 5/24* (2013.01); *G01D 5/243* (2013.01); *G01N 27/228* (2013.01); *G01N 27/048* (2013.01); *G01N 27/223* (2013.01)

(58) Field of Classification Search
CPC ............. G01N 27/028; G01N 27/048; G01N 27/121; G01N 27/22; G01N 27/221; G01N 27/223; G01N 27/225; G01N 27/227; G01N 27/228; G01N 2201/1214; G01N 2291/02845
USPC ....... 324/609, 640, 658, 663, 664, 667, 689; 73/74; 340/602, 604, 545.4; 361/178, 361/286
See application file for complete search history.

(56) References Cited

U.S. PATENT DOCUMENTS

| | | | | |
|---|---|---|---|---|
| 3,483,437 A | * | 12/1969 | Coyne .................. | H03K 17/955 331/110 |
| 3,636,444 A | * | 1/1972 | Strawn ................. | G01N 27/225 324/659 |
| 4,282,480 A | * | 8/1981 | Fujito .................. | G01N 27/046 324/659 |
| 4,319,185 A | * | 3/1982 | Hill ........................ | G01R 27/04 324/631 |
| 4,392,382 A | * | 7/1983 | Myers ..................... | G01L 9/125 73/708 |

(Continued)

FOREIGN PATENT DOCUMENTS

| | | | | |
|---|---|---|---|---|
| JP | 58-182502 | 10/1983 | | |
| JP | 2004-309501 A | * 11/2004 | ............. | G01N 27/04 |

OTHER PUBLICATIONS

European Search Report issued Jun. 25, 2013 in European 13151668.4, filed Jan. 17, 2013 (with English Translation).

*Primary Examiner* — Tung X Nguyen
*Assistant Examiner* — Sean Curtis
(74) *Attorney, Agent, or Firm* — Oblon, McClelland, Maier & Neustadt, L.L.P.

(57) ABSTRACT

The invention relates to a measuring circuit comprising a control block for controlling said circuit, a time base for providing a clock signal ($f_{clk}$) in order to time said circuit, a sensor block which is designed to provide an output signal, said measuring circuit comprising in addition a first counting block which is timed to the clock frequency and a second counting block which is timed by the frequency of the output signal of the sensor block.

20 Claims, 3 Drawing Sheets

(56) References Cited

U.S. PATENT DOCUMENTS

| | | | | |
|---|---|---|---|---|
| 4,517,622 A * | 5/1985 | Male | G01L 9/0073 | 361/283.1 |
| 4,743,836 A * | 5/1988 | Grzybowski | G01L 9/125 | 324/677 |
| 4,751,654 A * | 6/1988 | Lyyra | G01R 15/005 | 324/601 |
| 4,793,187 A * | 12/1988 | Kordts | G01D 3/032 | 702/93 |
| 5,123,035 A * | 6/1992 | Hottinger | G01D 5/243 | 377/20 |
| 5,291,534 A * | 3/1994 | Sakurai | G01D 3/0365 | 327/509 |
| 5,488,645 A * | 1/1996 | Mori | H04N 1/047 | 327/160 |
| 5,554,937 A * | 9/1996 | Sanders | G01R 27/2605 | 324/664 |
| 5,991,182 A * | 11/1999 | Novac | H02M 7/217 | 363/126 |
| 6,373,264 B1 * | 4/2002 | Matsumoto | G01D 5/24 | 324/658 |
| 6,433,524 B1 * | 8/2002 | Yang | G01R 17/105 | 323/274 |
| 6,509,804 B2 * | 1/2003 | Piazza | H03H 9/215 | 310/318 |
| 6,809,507 B2 * | 10/2004 | Morgan | A61B 5/042 | 204/403.14 |
| 6,930,917 B2 * | 8/2005 | Novac | H03B 5/36 | 365/185.05 |
| 7,030,709 B2 * | 4/2006 | Novac | H03B 5/364 | 331/116 FE |
| 7,598,821 B2 * | 10/2009 | Novac | H03B 5/04 | 331/109 |
| 7,804,307 B1 * | 9/2010 | Bokma | G01R 27/2605 | 324/607 |
| 8,330,603 B1 * | 12/2012 | Gibb | G01F 23/266 | 340/602 |
| 8,760,302 B1 * | 6/2014 | MacDonald | G01F 25/0061 | 340/602 |
| 8,909,847 B2 * | 12/2014 | Novac | G04D 7/003 | 711/103 |
| 2005/0087620 A1 * | 4/2005 | Bowers | A01G 25/167 | 239/63 |
| 2008/0100350 A1 * | 5/2008 | Pernia | H03L 5/00 | 327/114 |
| 2009/0322351 A1 * | 12/2009 | McLeod | G06F 3/0416 | 324/658 |
| 2010/0271144 A1 * | 10/2010 | McCorquodale | H03B 5/04 | 331/117 FE |
| 2011/0316558 A1 * | 12/2011 | Pfaffinger | G01D 5/2216 | 324/603 |
| 2013/0009652 A1 * | 1/2013 | Lu | G01D 5/2415 | 324/658 |
| 2015/0130482 A1 * | 5/2015 | van Lammeren | G01N 27/221 | 324/682 |
| 2015/0130648 A1 * | 5/2015 | Krau | H03M 1/442 | 341/156 |

* cited by examiner

US 9,494,542 B2

CONTROL SYSTEM AND METHOD FOR SENSOR MANAGEMENT

This application claims priority from European Patent application No. 13151668.4 filed Jan. 17, 2013, the entire disclosure of which is hereby incorporated by reference.

The present invention relates to a measuring circuit comprising a control block for controlling said circuit, a time base for providing a clock signal in order to time said circuit, a sensor block which is designed to provide an output signal, said measuring circuit comprising in addition a first counting block which is timed to the clock frequency and a second counting block which is timed by the frequency of the output signal of the sensor block.

TECHNOLOGICAL BACKGROUND

Humidity sensors are formed by two armatures, each provided with a plurality of arms. The two armatures are designed to be interleaved with each other and have a dielectric between each other. These armatures are supplied with voltage so that their interleaving causes the creation of a capacitance.

This humidity sensor functions such that, when the degree of moisture in the air increases, molecules of water infiltrate between the two armatures into the dielectric. This infiltration of water causes a modification in the capacitance which makes it possible to quantify the degree of moisture during a measurement by applying a voltage. The humidity sensor can be a structure connected to an integrated circuit or be directly included in the integrated circuit.

Several methods are known for determining a humidity value from this capacitance.

A first method consists of connecting, at the output of the humidity sensor, a charge amplifier in order to obtain a voltage signal which is representative of the degree of moisture. This signal is sent to a signal conditioner which prepares the signal to be sent to an analogue-digital converter so as to provide a numerical value N. This numerical value N is then sent to a circuit which linearises it because the curve of the capacitance as a function of the degree of moisture is not linear. A numerical value N which is a function of the capacitance C of the sensor is then obtained.

A second method consists of connecting, at the output of the humidity sensor, a circuit in order to obtain a frequency signal which is representative of the degree of moisture. In fact, this variable capacitance is inserted in a resonator so as to produce an RC oscillator. Consequently, the frequency output from said resonator is dependent upon the value of the capacitance and therefore upon the degree of moisture. This frequency is sent to a signal conditioner which prepares the signal to be sent to an analogue-numerical converter so as to provide a numerical number N. This signal conditioner can be a numerical frequency demodulator or an assembly formed by a circuit which makes it possible to convert this frequency signal into voltage then to convert it into a numerical value N which will be processed in order to obtain the value of the physical quantity.

A disadvantage of these two methods is that they require a circuit which comprises a large number of components, i.e. a circuit, the manufacturing cost of which is high but also which requires a larger silicon surface during integration in an integrated circuit. For this reason, the number of measuring circuits per circuit board is less.

SUMMARY OF THE INVENTION

The aim of the invention is to remedy the disadvantages of the prior art by proposing to provide a measuring circuit which is precise whatever components are used and which is less expensive, in particular during implementation in an integrated circuit.

To this end, the invention relates to a measuring circuit comprising a control block for controlling said circuit, a time base for providing a clock signal in order to time said circuit, a sensor block which is designed to provide an output signal, said measuring circuit comprising in addition a first counting block which is timed to the clock frequency and a second counting block which is timed by the frequency of the output signal of the sensor block, characterised in that the sensor block is designed to provide, as output signal, a first signal, the frequency of which is representative of the measured physical quantity or a second signal, the frequency of which is a reference frequency and in that the control block controls the measuring circuit so that the first and second counting blocks work according to a first phase in which the first and second counting blocks count and a second phase in which the first counting block counts and the second counting block counts down and in that the timing frequency of the second counting block during the first phase is different from that during the second phase.

In a first advantageous embodiment, the second counting block is timed by the frequency of the second signal during the first phase and by the frequency of the first signal during the second phase.

In a second advantageous embodiment, the control block comprises a control circuit and a sequencer block.

In a third advantageous embodiment, the second counting block comprises a zero detector connected to the sequencer block.

In another advantageous embodiment, the sensor block comprises an oscillator, a first variable-value electronic component and a second fixed-value electronic component, the first and the second electronic component being connected in parallel to the oscillator by means of commutation means and in that the first electronic component makes it possible to provide the first signal and in that the second electronic component makes it possible to provide the second signal.

In another advantageous embodiment, the first component and the second component each comprise a first terminal and a second terminal and in that the commutation means comprise a first and a second controllable switch, which are connected in series between the first terminal of the first component and the first terminal of the second component and a third and a fourth controllable switch, which are connected in series between the second terminal of the first component and the second terminal of the second component, the connection point between the first and the second controllable switch and the connection point between the third and the fourth controllable switch being connected to the oscillator unit.

In another advantageous embodiment, the first component and the second component are capacitors.

In another advantageous embodiment, the first component and the second component are resistors.

In another advantageous embodiment, the first component and the second component are inductance coils.

In another advantageous embodiment, the sensor block is able to measure the degree of moisture.

In another advantageous embodiment, it comprises in addition a linearization circuit.

The invention likewise relates to a method for management of a measuring circuit comprising a control block for controlling said circuit, a resonator for providing a clock signal in order to time said circuit, a sensor block which is designed to provide an output signal, said measuring circuit comprising in addition a first counting block which is timed to the clock frequency and a second counting block which is timed by the frequency of the output signal of the sensor block, characterised in that the sensor block is designed to provide, as output signal, a first signal, the frequency of which is representative of the measured physical quantity or a second signal, the frequency of which is a reference frequency and in that said method comprises the following steps:

1) selecting the second signal, the frequency of which is a reference frequency as output signal of the sensor block;

2) starting the counting of the first counting block which is timed by the clock signal and of the second counting block which is timed by the output signal of the sensor block;

3) when the first counting block reaches a first predefined number, it is reset at zero and the second counting block stops counting;

4) selecting the first signal, the frequency of which is representative of the measured physical quantity as output signal of the sensor block;

5) starting the counting of the first counting block which is timed by the clock signal and the counting down of the second counting block from the value counted during step 3), said second counting block being timed by the output signal of the sensor block;

6) when the second counting block reaches a second predefined number:
   stopping the counting of the first counting block and the counting down of the second counting block and
   saving the value counted by the first counting block;

7) determining, from the value counted by the first counting block, the value of the physical quantity measured by the sensor block.

In another advantageous embodiment, the second predefined number is zero.

In another advantageous embodiment, the first predefined number is dependent upon the resolution of the counter.

In another advantageous embodiment, it comprises in addition a final step which is intended to linearise the value counted by the first counting block as a function of the measured physical quantity, this step consisting of squaring said value counted by the first counting block.

The invention relates in addition to a wearable electronic object comprising the measuring circuit according to the invention.

BRIEF DESCRIPTION OF THE FIGURES

The aims, advantages and features of the measuring circuit according to the present invention will appear more clearly in the following detailed description of at least one embodiment of the invention, given solely by way of non-limiting example and illustrated by the annexed drawings in which.

DETAILED DESCRIPTION

Figure 1:
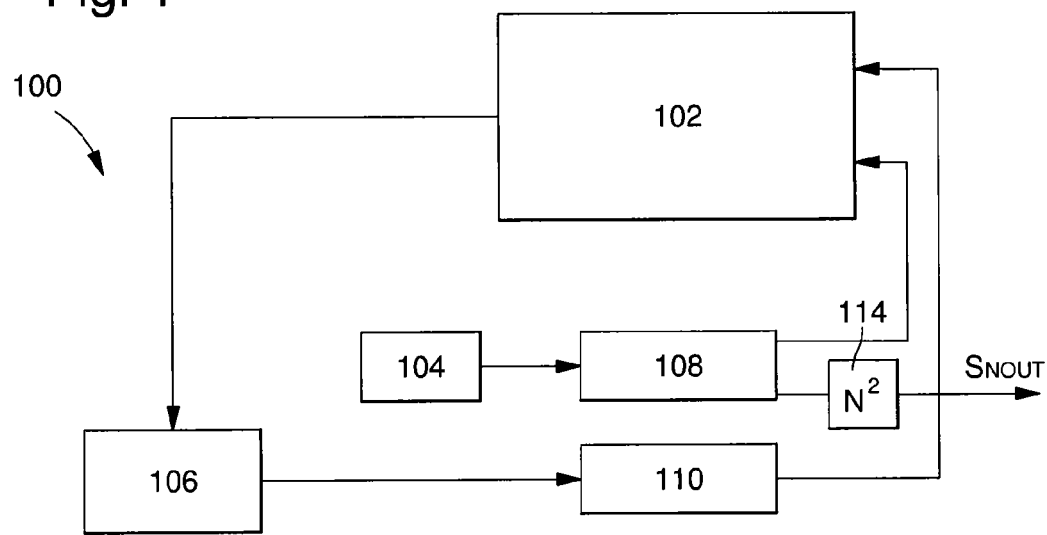
FIGS. 1 and 2 represent schematically an example of a measuring circuit according to the present invention.
Figure 2:
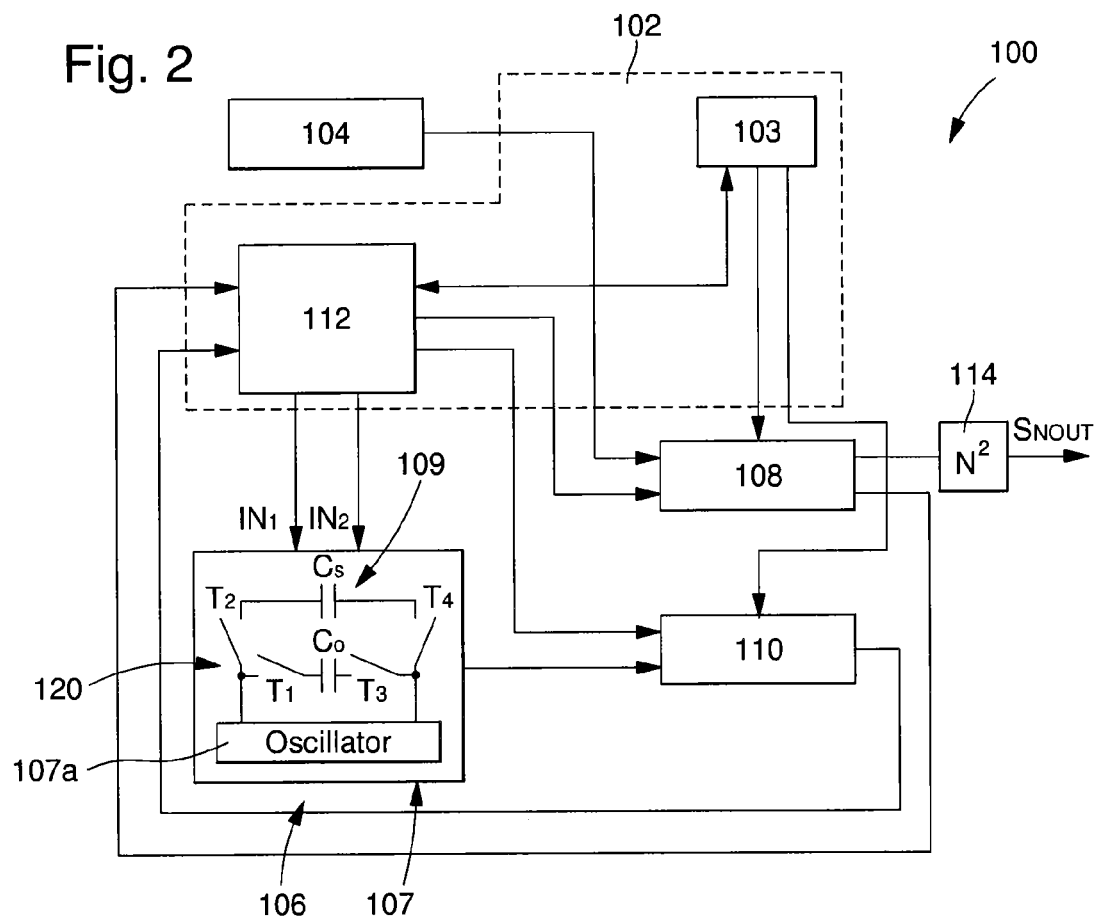

FIGS. 1 and 2 represent the measuring circuit 100 according to the invention. This measuring circuit 100 can be integrated in a wearable/portable object, such as a watch or a telephone or communication apparatus or a portable measuring apparatus. This measuring circuit 100 comprises a control block 102 comprising a control circuit 103 which is used to control the measuring circuit 100. The measuring circuit 100 is timed by a time base 104 which can be for example an RC oscillator or a quartz oscillator and which provides an Fclk signal.

This measuring circuit 100 comprises in addition a sensor block 106 for providing an indication of a physical quantity. In the present case, the sensor block 106 is used to measure the degree of moisture. The sensor block 106 comprises a humidity sensor or unit for measuring humidity 109. This humidity sensor 109 has the form of a micromechanism of the MEMS type, composed of two electrically supplied armatures. When the humidity increases, molecules of water infiltrate between the armatures so that the capacitance between these varies. The humidity sensor 109 will be represented by a variable capacitor Cs comprising a first contact terminal and a second contact terminal.

Advantageously according to the invention, the sensor block 106 comprises, in addition to the sensor 109, an oscillator unit 107 comprising a reference capacitor $C_0$ and an RC oscillator 107a. The reference capacitor $C_0$ comprises a first contact terminal and a second contact terminal. The first contact terminal of the capacitor $C_0$ is connected to the first contact terminal of the humidity sensor via commutation means 120, as a first T1 and a second T2 controllable switch. The second contact terminal of the capacitor $C_0$ is connected to the second contact terminal of the humidity sensor via commutation means, as a third T3 and a fourth T4 controllable switch. The controllable switches can be transistors. This configuration makes it possible to connect the reference capacitor $C_0$ or the variable capacitor $C_s$ acting as humidity sensor to the RC oscillator 107a. This RC oscillator 107a works on the principle of an RC circuit made to oscillate, the frequency being dependent upon the value of the resistance R and upon the value of the capacitance of the capacitor C so that the frequency of an RC oscillator equals:

$$f = \frac{1}{4\pi}\sqrt{\frac{gm}{R \cdot Cs * CL}}$$

with gm which is the transconductance of the MOS transistors N3 and N4 and $C_L$ an internal charge capacitance.

Figure 4:
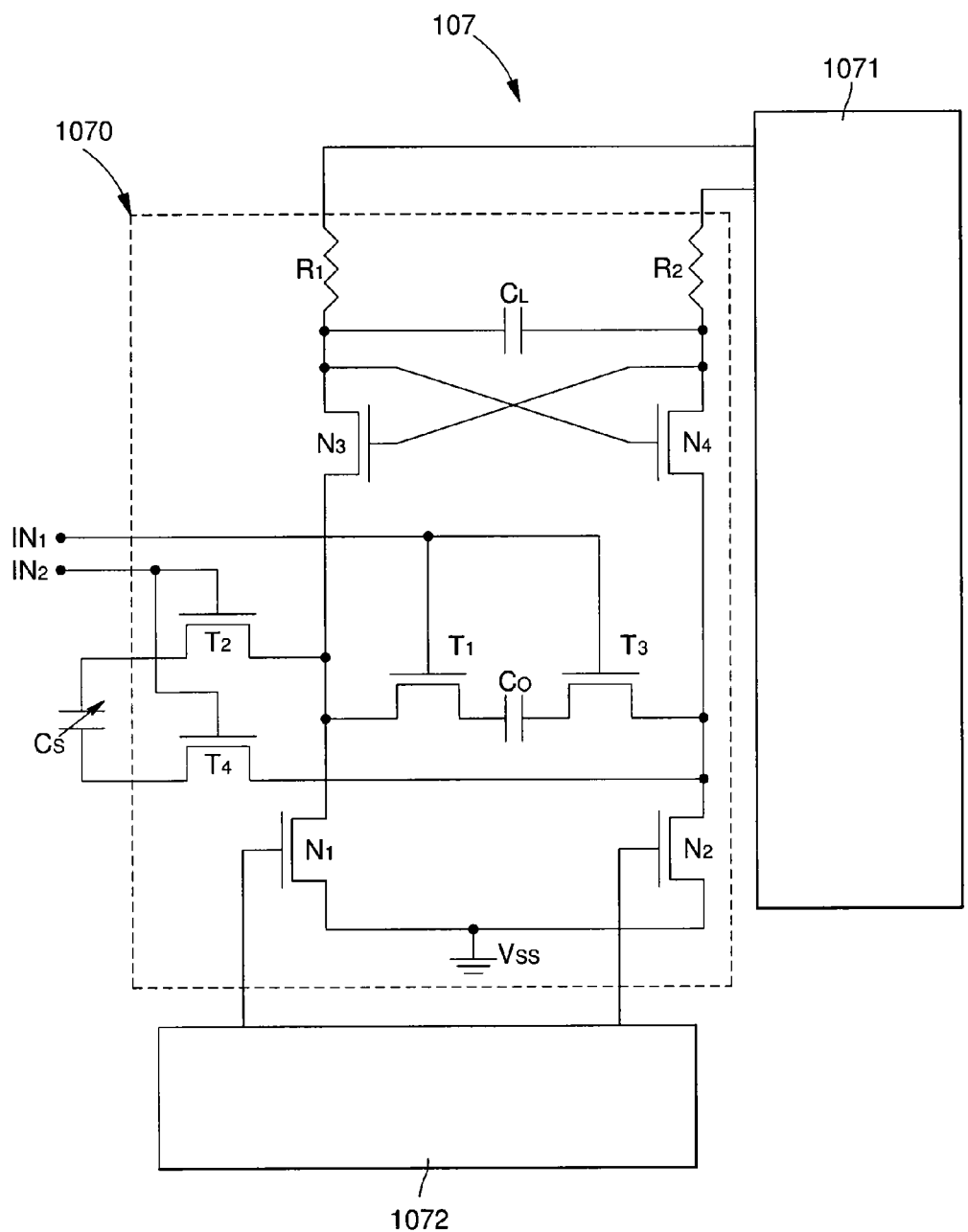
FIG. 4 represents schematically the oscillator unit according to the invention.

In the case of the present invention, the RC oscillator unit 107 comprises three elements, i.e. a sweep oscillator 1070 connected to a polarisation block 1072 and a clock extractor block 1071, as can be seen in FIG. 4. The sweep oscillator comprises two pairs of transistors, a first pair of transistors N1 and N2, each having their source connected to the earth of the circuit and the drain connected to the source of a transistor. The drain of the transistor N1 is connected to the source of the transistor N3 and the drain of the transistor N2 is connected to the source of the transistor N4. The drains of the transistors N3 and N4 are each connected to one terminal of a resistor which has its other terminal connected to a supply voltage via the extractor module. The gates of the transistors N1 and N2 are connected to the polarisation block whilst the gate of the transistor N3 is connected to the drain of the transistor N4, the gate of the transistor N4 being connected to the drain of the transistor N3.

The sweep oscillator likewise comprises four commutation transistors (T1, T2, T3 and T4) which are the commutation means 120. The transistors T1 and T3 are designed so that the drain of T1 is connected to the drain of N1 and so that the source of T3 is connected to the drain of N2, the capacitance $C_0$ being connected between the source of T1 and the drain of T3. The transistors T2 and T4 are connected so that the source of T2 is connected to the drain of N1 and so that the source of T4 is connected to the drain of N2. The gates of T1 and T3 are connected to a first terminal IN1 and the gates of T2 and T4 are connected to a second terminal IN2 so as to be able to be commutated. The structure of the sensor, i.e. the variable capacitance Cs, is connected between the drains of T2 and T4. It is noted that the sweep oscillator has an internal capacitance $C_L$ between the terminal of the resistor R1 which is connected to the transistor N3 and the terminal of the resistor R2 which is connected to the transistor N4. There is obtained a frequency:

$$f = \frac{1}{4\pi}\sqrt{\frac{gm}{R \cdot Cs * CL}}$$

For this reason, the frequency provided at the output of the sensor block 106 will be dependent upon the capacitance of the variable capacitor $C_s$, in order to give a first frequency signal $F_s$ which is representative of the measured physical quantity, or of the reference capacitor $C_0$ in order to give a second frequency signal $F_{ref}$ which is a reference signal.

Figure 3:
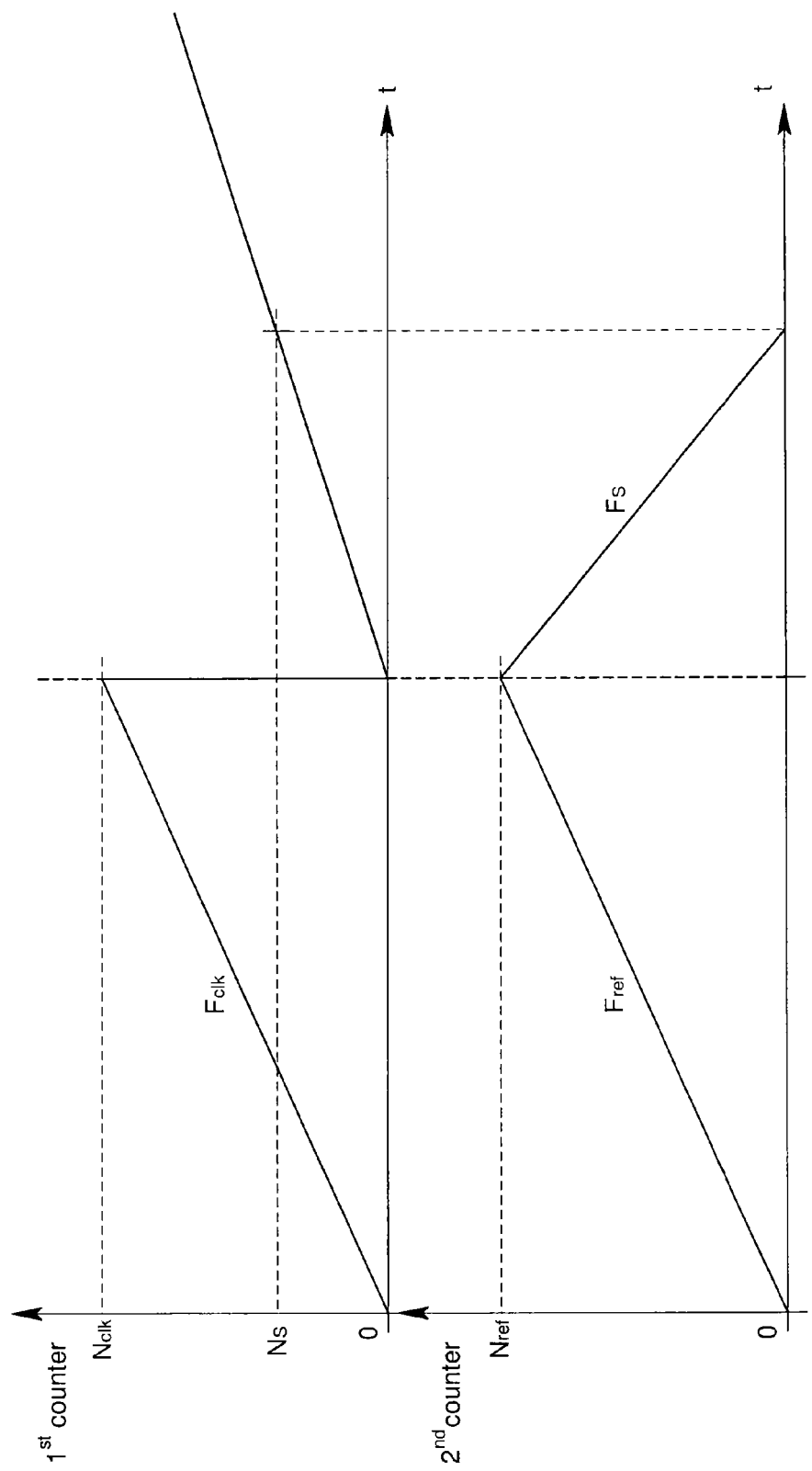
FIG. 3 represents an operational diagram of the method according to the invention.

Furthermore, the measuring circuit 100 comprises a first counting block 108 which is connected to the time base 104 and a second counting block 110 which is connected to the output of the sensor block 106. The first counting block 108 and the second counting block 110 are synchronised, i.e. they are controlled simultaneously. In order to control the first 108 and the second 110 counting block, the control circuit 103 is used. The control block 102 comprises a unit for synchronisation of the counters. The control block 102 comprises in addition a sequencer block 112. This sequencer block 112 is used to act, at the same time, on the first 108 and second 110 counting blocks but also on the sensor block 106. This configuration makes it possible to use a method for calculating the physical quantity according to the invention. This method is termed double gradient method. This method proceeds in two phases, a diagram of which can be seen in FIG. 3.

In a first phase, the control circuit 103 and the sequencer block 112 control the measuring circuit 100. The sequencer block 112 controls the sensor block so that the output frequency of the sensor block 106 is the reference frequency $F_{ref}$, i.e. the sequencer block 112 ensures that the second T2 and fourth T4 switches are open when the first T1 and third T3 switches are closed.

Furthermore, the control circuit 103 and the sequencer block 112 control the measuring circuit 100 so that the first counting block 108 and the second counting block 110 begin to count. The first counting block 108 counts by being timed by the frequency of the time base $F_{clk}$ while the second counting block 110 counts by being timed by the output frequency of the sensor block, i.e. the reference frequency $F_{ref}$. The first counting block 108 is configured to count up to a first predefined number $N_{clk}$. The second counting block 110 is synchronous with the first counting block, i.e. the first counting block 108 and the second counting block 110 begin to count or start simultaneously. When the first counter reaches the predefined number $N_{clk}$, it stops counting and the second counting block 110 likewise stops counting.

Once the first counting block 108 has reached the predefined number $N_{clk}$ and has changed to zero, the second phase can begin. This change to zero is detected by the control circuit 103. This control circuit 103 and the sequencer block 112 act on the second counting block 110 so that the latter changes from a counting mode to a counting down mode.

This phase consists firstly of permuting the output frequency of the sensor block 106. The sequencer block 112 acts such that the second T2 and fourth T4 switches are closed when the first T1 and third T3 switches are open.

The output frequency is therefore dependent upon the physical quantity measured by the sensor.

Then, in this second phase, the first counting block 108 begins again to count whilst the second counting block 110 begins to count down. The second counting block 110 begins to count down from the saved number $N_{ref}$. The count down takes place then by being timed by the output frequency of the sensor block 106, i.e. the frequency representative of the measured physical quantity $F_s$. Each counting block is provided with a zero detector so that when the second counting block 110 reaches a second predefined number which is zero, the first counter 108 stops counting also. The number $N_s$ which is counted by the first counter 108 is then saved.

The various values of $N_{ref}$, $N_{clk}$ and the values of the various frequencies make it possible to calculate the value of the physical quantity. These values are transmitted to the control circuit 103 or to a calculation circuit, not represented in the Figures, which has the task of providing the value of the measured physical quantity.

In fact, from the first phase, it is accepted that $$N_{clk} \times \frac{1}{Fclk} = N_{ref} \times \frac{1}{Fref}$$

For this reason:

$$N_{clk} \times \frac{Fref}{Fclk} = N_{ref} \quad \text{(Equation 1)}$$

Then, from the second phase, it is accepted that:

$$N_s \times \frac{1}{Fclk} = N_{ref} \times \frac{1}{Fs} \quad \text{(Equation 2)}$$

By combining equations 1 and 2, there is therefore obtained:

$$N_s = N_{ref} \times \frac{Fclk}{Fs} = N_{clk} \times \frac{Fref}{Fclk} \times \frac{Fclk}{Fs} = N_{clk} \times \frac{Fref}{Fs} \quad \text{(Equation 4)}$$

By knowing the formulae of the frequencies of the RC oscillators for the frequencies $F_{ref}$ and $F_s$, these formulae can be introduced into equation 4 which gives:

$$N_s = N_{clk} \times \sqrt{\frac{Cs}{C0}}$$

Therefore a number $N_s$ which is independent of the frequency of the time base is obtained. This confers the advantage of having a circuit, the frequency of the time base 104 of which does not then need to be precise because it has no influence on the measured value.

In order to linearize the relation between the capacitance measured by the sensor and the number $N_s$ given by the counter 108, the number $N_s$ is squared by a linearization circuit 114 in order to obtain the number $N_{sl}$ which gives:

$$N_{sl} = N_s^2 = N_{clk}^2 \times \frac{Cs}{C0}$$

This linearization circuit 114 provides, at the output $S_{NOUT}$, the number $N_{sl}$ ready to be used by a processor for example.

Now the number $N_{clk}$ is dependent upon the resolution of the circuit. In fact, the data provided by the counting blocks 108, 110 are transmitted on a given bit number, since the greater the bit number, the greater is the precision. Which means that the number $N_{clk}$ is equal to $2^{resolution}$ with the resolution which is equal to the bit number used.

Consequently, $$N_{sl} = N_{clk}^2 \times \frac{Cs}{C0} = 2^{2 \times resolution} \times \frac{Cs}{C0}$$

It is therefore noted that the number $N_{sl}$ which makes it possible to obtain the value of the measured physical quantity is independent of the frequency of the measuring circuit 100 but also independent of the resistance R of the RC oscillator 107a of the sensor block 106 or of the transconductance $g_m$ of the transistors of the oscillator 107a and of the internal capacitance $C_L$ of the oscillator 107a.

Now, via a prior step during manufacture of the sensor block 106, a standardisation is effected so that the capacitance $C_s$ for a degree of moisture of 0% is defined and so that the capacitance $C_s$ for a degree of moisture of 100% is defined. For this reason, it is defined that the number $N_{clk}$ squared corresponds to the maximum degree of moisture and by rapid calculation, the degree of moisture can be determined as a function of the measured number $N_{sl}$.

It is conceivable that this method is used on an ad hoc basis. There is meant by this that the first and second phases can be effected at a regular interval in order to have a measurement of the physical quantity at a regular interval. This measuring frequency can be defined or given a parameter. Likewise, it is possible that this measurement of the physical quantity using the method and the circuit according to the invention is performed on demand. It is understood that the user activates a command when he wants to know the value of the physical quantity.

In a variant, the measuring circuit 100 will not be limited to a sensor block 106 for measuring the degree of moisture and will be extended to other physical quantities which can be measured with a capacitive sensor.

In an alternative, the sensor block 106 will not be capacitive but inductive. Because of this, the sensor will comprise a structure acting as variable inductance which will be connected to an oscillator of the LC type for example. Likewise, a sensor using a variable resistor might be used, said variable resistor being connected to an RC oscillator.

The invention claimed is:

1. A measuring circuit, comprising:
    a control block configured to control said circuit;
    a time base configured to provide a clock signal ($f_{clk}$) in order to time said circuit;
    a sensor block comprising an oscillator, a first variable-value electronic component ($C_s$), and a second fixed-value electronic component ($C_0$), the sensor block being configured to provide an output signal;
    a first counting block, which is timed to a clock frequency; and
    a second counting block, which is timed by a frequency of the output signal of the sensor block,
    wherein the first variable-value electronic component ($C_s$) and a second fixed-value electronic component ($C_0$) each comprise a first terminal and a second terminal, and are connected in parallel to the oscillator by means of commutation means,
    wherein the first variable-value electronic component ($C_s$) is configured to provide a first signal, and the second fixed-value electronic component ($C_0$) is configured to provide a second signal,
    wherein the commutation means comprises a first controllable switch (T1) and a second controllable switch (T2), which are connected in series between the first terminal of the first variable-value electronic component ($C_s$) and the first terminal of the second fixed-value electronic component ($C_0$),
    wherein the sensor block is further configured to provide, as the output signal,
        the first signal, a frequency of which is representative of a measured physical quantity, or
        the second signal, a frequency of which is a reference frequency,
    wherein the control block is further configured to control the measuring circuit so that the first and second counting blocks function according to a first phase, in which the first and second counting blocks count, and a second phase, in which the first counting block counts and the second counting block counts down, and
    wherein a timing frequency of the second counting block during the first phase is different from that during the second phase.

2. The measuring circuit according to claim 1, wherein the second counting block is timed by a frequency ($F_{ref}$) of the second signal during the first phase and by a frequency ($F_s$) of the first signal during the second phase.

3. The measuring circuit according to claim 1, wherein the control block comprises a control circuit and a sequencer block.

4. The measuring circuit according to claim 2, wherein the control block comprises a control circuit and a sequencer block.

5. The measuring circuit according to claim 3, wherein the second counting block comprises a zero detector connected to the sequencer block.

6. The measuring circuit according to claim 4, wherein the second counting block comprises a zero detector connected to the sequencer block.

7. The measuring circuit according to claim 1,
    wherein the commutation means further comprises a third controllable switch (T3) and a fourth controllable switch (T4), which are connected in series between the second terminal of the first variable-value electronic component ($C_s$) and the second terminal of the second fixed-value electronic component ($C_0$), and
    wherein a connection point between the first controllable switch (T1) and the second controllable switch (T2), and the connection point between the third controllable switch (T3) and the fourth controllable switch (T4), are connected to the oscillator.

8. The measuring circuit according to claim 1, wherein the first component and the second component are capacitors.

9. The measuring circuit according to claim 7, wherein the first component and the second component are capacitors.

10. The measuring circuit according to claim 1, wherein the first component and the second component are resistors.

11. The measuring circuit according to claim 7, wherein the first component and the second component are resistors.

12. The measuring circuit according to claim 1, wherein the first component and the second component are inductance coils.

13. The measuring circuit according to claim 7, wherein the first component and the second component are inductance coils.

14. The measuring circuit according claim 1, wherein the sensor block is configured to measure a degree of moisture.

15. The measuring circuit according to claim 1, further comprising a linearization circuit.

16. A method for management of a measuring circuit, the measuring circuit comprising:
- a control block configured to control said circuit,
- a time base configured to provide a clock signal in order to time said circuit,
- a sensor block comprising an oscillator, a first variable-value electronic component ($C_s$), and a second fixed-value electronic component ($C_0$), the sensor block being configured to provide an output signal,
- a first counting block, which is timed to a clock frequency, and
- a second counting block, which is timed by a frequency of the output signal of the sensor block,
- wherein the first variable-value electronic component ($C_s$) and a second fixed-value electronic component ($C_0$) each comprise a first terminal and a second terminal, and are connected in parallel to the oscillator by means of commutation means,
- wherein the first variable-value electronic component ($C_s$) is configured to provide a first signal, and the second fixed-value electronic component ($C_0$) is configured to provide a second signal,
- wherein the commutation means comprises a first controllable switch (T1) and a second controllable switch (T2), which are connected in series between the first terminal of the first variable-value electronic component ($C_s$) and the first terminal of the second fixed-value electronic component ($C_0$),
- wherein the sensor block is further configured to provide, as the output signal, the first signal, a frequency ($F_s$) of which is representative of a measured physical quantity, or the second signal, a frequency ($F_{ref}$) of which is a reference frequency; and the method the following steps:
1) selecting the second signal as the output signal of the sensor block;
2) starting counting of the first counting block and of the second counting block;
3) when the first counting block reaches a first predefined number ($N_{clk}$), resetting the first counting block to zero and stopping the counting of the second counting block;
4) selecting the first signal as the output signal of the sensor block;
5) starting the counting of the first counting block and the counting down of the second counting block from a value ($N_{ref}$) counted during step 3), said second counting block being timed by the output signal of the sensor block;
6) when the second counting block reaches a second predefined number:
   stopping the counting of the first counting block and the counting down of the second counting block, and
   saving a value ($N_s$) counted by the first counting block; and
7) determining, from the value ($N_s$), a value of the physical quantity measured by the sensor block.

17. The method for management according to claim 16, wherein the second predefined number is zero.

18. The method for management according to claim 16, wherein the first predefined number ($N_{clk}$) is dependent upon a resolution of the counter.

19. The method for management according to claim 16, further comprising linearizing a value counted by the first counting block as a function of the measured physical quantity by squaring said value counted by the first counting block.

20. A wearable/portable electronic object comprising the measuring circuit according to claim 1.

* * * * *